(12) United States Patent
Ziganshin et al.

(10) Patent No.: US 9,649,033 B2
(45) Date of Patent: May 16, 2017

(54) DEVICE FOR REMOTE NON-CONTACT MONITORING OF VITAL SIGNS OF A LIVING BEING

(71) Applicant: NanoPulse, Inc., Moscow (RU)

(72) Inventors: Eduard Gusmanovich Ziganshin, Moskovskaya obl. (RU); Mikhail Andreevich Numerov, Saint-Petersburg (RU)

(73) Assignee: Nanopulse, Inc. (RU)

( * ) Notice: Subject to any disclaimer, the term of this patent is extended or adjusted under 35 U.S.C. 154(b) by 234 days.

(21) Appl. No.: 14/430,430

(22) PCT Filed: Sep. 20, 2013

(86) PCT No.: PCT/RU2013/000819
§ 371 (c)(1),
(2) Date: Mar. 23, 2015

(87) PCT Pub. No.: WO2014/046573
PCT Pub. Date: Mar. 27, 2014

(65) Prior Publication Data
US 2015/0208920 A1    Jul. 30, 2015

(30) Foreign Application Priority Data

Sep. 21, 2012   (RU) ............... 20120140602

(51) Int. Cl.
*H04Q 9/00*   (2006.01)
*A61B 5/00*   (2006.01)
(Continued)

(52) U.S. Cl.
CPC .......... *A61B 5/0002* (2013.01); *A61B 5/0015* (2013.01); *A61B 5/05* (2013.01);
(Continued)

(58) Field of Classification Search
CPC ....... A61B 5/01; A61B 5/02055; A61B 5/746; A61B 5/0002; A61B 5/0022; A61B 5/0205
(Continued)

(56) References Cited

U.S. PATENT DOCUMENTS 7,493,663 B2   2/2009   Gorsen
7,725,150 B2   5/2010   Tupin, Jr. et al.
(Continued)

FOREIGN PATENT DOCUMENTS

EP   0984299 A1   3/2000
EP   1724684 A1   11/2006
(Continued)

OTHER PUBLICATIONS

Extended European Search Report dated Jul. 7, 2016, Application No./Patent No. 13838704.8-1657/2907448 PCT/RU2013000819—(8) pages.
(Continued)

*Primary Examiner* — Kerri McNally
*Assistant Examiner* — Sharmin Akhter
(74) *Attorney, Agent, or Firm* — Boyle Frerickson, SC

(57) ABSTRACT

The present disclosure relates to a device for remote non-contact monitoring of vital signs of a living being. The present disclosure enables improved measurement accuracy and reliability, increased operating range and reduced likelihood of mistakenly detecting extraneous objects. The device comprises at least one measuring unit, at least one control and data processing unit, and at least one interface unit, connected to each other. The measuring unit comprises a radio transmitting module and a radio receiving module. The control and data processing unit is configured to generate control pulses for each of the radio transmitting and radio receiving modules delayed for arbitrary time periods
(Continued)

between each other, and is additionally configured to generate control pulses of arbitrary duration for each of the radio transmitting and radio receiving modules. Each radio transmitting module and/or each radio receiving module contained in the measuring unit is made independent of the other modules.

20 Claims, 2 Drawing Sheets

(51) Int. Cl.
| | |
|---|---|
| *G01S 7/41* | (2006.01) |
| *G01S 13/02* | (2006.01) |
| *G01S 13/88* | (2006.01) |
| *A61B 5/05* | (2006.01) |
| *A61B 5/08* | (2006.01) |
| *A61B 5/11* | (2006.01) |
| *A61B 5/113* | (2006.01) |

(52) U.S. Cl.
CPC ............ *A61B 5/1118* (2013.01); *A61B 5/746* (2013.01); *G01S 7/41* (2013.01); *G01S 13/0209* (2013.01); *G01S 13/88* (2013.01); *A61B 5/0816* (2013.01); *A61B 5/113* (2013.01); *A61B 5/1115* (2013.01); *A61B 5/4809* (2013.01); *A61B 2503/04* (2013.01)

(58) Field of Classification Search
USPC .... 340/286.07, 573.1–576, 870.07; 600/301, 600/508, 509, 513, 514, 527, 534; 382/128
See application file for complete search history.

(56) References Cited

U.S. PATENT DOCUMENTS

| | | | |
|---|---|---|---|
| 8,834,364 B2 | 9/2014 | Heneghan et al. | |
| 2001/0009404 A1* | 7/2001 | Paese ..................... | E03C 1/057 342/28 |
| 2006/0217612 A1* | 9/2006 | Ouchi .................... | A61B 5/024 600/407 |
| 2009/0203972 A1 | 8/2009 | Heneghan et al. | |
| 2009/0209850 A1* | 8/2009 | Tao ........................ | A61B 5/024 600/425 |
| 2009/0238513 A1 | 9/2009 | Hao et al. | |
| 2010/0204550 A1 | 8/2010 | Heneghan et al. | |
| 2011/0178377 A1 | 7/2011 | Heneghan et al. | |

FOREIGN PATENT DOCUMENTS

| | | |
|---|---|---|
| EP | 2369515 A1 | 9/2011 |
| RU | 71165 U1 | 2/2008 |
| RU | 2369323 C1 | 10/2009 |
| RU | 2462990 C2 | 11/2011 |
| WO | 2008001092 A2 | 1/2008 |
| WO | 2011146517 A2 | 11/2011 |

OTHER PUBLICATIONS

International Search Report and the Written Opinion of the International Searching Authority; Application No. PCT/RU2013/000819—mailed Feb. 13, 2014—(7) pages.

* cited by examiner

DEVICE FOR REMOTE NON-CONTACT MONITORING OF VITAL SIGNS OF A LIVING BEING

CROSS-REFERENCE TO RELATED APPLICATIONS

This application claims priority to International Application No. PCT/RU2013/000819, filed on Sep. 20, 2013, which claims priority to Russian Patent Application No. RU2012140602, filed on Sep. 21, 2012, the entire contents of which are incorporated herein by reference.

BACKGROUND OF THE INVENTION

Field of the Invention

The present disclosure generally relates to the field of medicine, and more particularly, to devices for remote non-contact monitoring of vital signs of a living being, such as motion, breathing and heartbeat, enabling the health status of the organism to be monitored continuously throughout the monitoring time, and to determine its state of wakefulness, sleep, waking from sleep, convulsions, respiratory arrest.

Description of Related Art

Every year devices for remote non-contact monitoring of vital signs of living beings, in particular, human beings, becoming increasingly relevant, as their use in various fields of medicine allows impact on the subject of observation and control to be minimized, and at the same time improving the information content and accuracy of control and diagnostics.

The U.S. patent application Ser. No. 20090203972, IPC A61B 5/00, publ. 13 Aug. 2009 describes an apparatus for remote non-contact monitoring of breathing, heart rate and motion, comprising a processor configured to analyze the signal reflected by a subject without physical contact with the subject, and take measurements of breathing, heart rate and motion of the subject from the reflected signal, and a display configured to provide analyzed and measured parameters to a local or remote user of the apparatus. The apparatus further comprises a sensor coupled to the processor and arranged to receive the signal reflected from the subject. The sensor and processor are both arranged to operate without any direct or indirect physical contact with the subject. The reflected signal is generated by a transmitter collocated with the apparatus. The transmitter is configured to generate a radio-frequency energy signal compatible for use with a living subject. The reflected signal is multiplied with the transmitted signal to output a modulated signal representing a respiration, cardiac and/or motion function.

A disadvantage of the apparatus is the use of the single signal both for transmission and as a reference signal for the multiplier. This either means the use of continuous probing and the reference signal, which automatically leads to a signal reflected from extraneous subjects and interference being received, or limits the distance resolution of the apparatus by the length of the UWB (Ultra Wide Band) signal (i.e., ultra wideband signal) or makes it impossible for the probing signal to comply with the UWB standards that will in all likelihood require a license to use the spectrum band. The U.S. Pat. No. 7,725,150, IPC A61B 5/05 G01S, publ. 25 May 2010, discloses a system for extracting physiological data using an ultra wideband signal comprising a controller connected to the user interface, a first signal processor input, a first analog-to-digital converter input, a first delay range input, and a pulse repetition frequency generator. The first output of the pulse repetition frequency generator is connected to the transmitter input, the output of which is connected to a receiving-transmitting antenna. The second output of the generator is connected to the second input of the delay range, the output of which is connected to the first input of the receiver. The second input of the receiver is connected to the receiving-transmitting antenna, and its output is connected to the second input of the analog-to-digital converter. Output of the analog-to-digital converter is connected to the second input of signal processor, the output of which is connected to the user interface.

A disadvantage of this device is in broadcasting radio frequency pulse signals without radiofrequency content, which makes the device inefficient from an energy point of view.

Prior art reveals systems for monitoring parameters of vital signs of living beings, including non-contact motion, breathing and heart rate sensors (WO2010091168, publ. 12 Aug. 2010, IPC A61B 5/0205, A61B 5/113; WO2010036700, publ. 1 Apr. 2010 IPC G06 F 19/00; WO2008057883, publ. 15 Sep. 2008, IPC A61B 5/00; WO2007143529, publ. 13 Dec. 2007, IPC A41D 27/00 27/02 27/12 27/28 13/00, G21F 3/02). In the above systems, the sensor is a typical radar comprising a continuous or pulsed probing signal generator, a transmitting antenna, a receiving antenna, an amplifier, a mixer and a frequency filter. Disclosed are modifications of radar using short-pulse UWB signals and the Doppler Effect. All these radars, if no original solution is implemented, are limited in resolution, range of the device, as well as of the noise tolerance.

The nearest selected analog (prototype) is a pulsed ultra-wideband sensor (patent of the Russian Federation No. 2369323, IPC A61B 5/08 G01S 13/00, publ. 10 Oct. 2009) for measuring respiratory rate and heart rate. The sensor can be used as a highly sensitive diagnostic tool for the cardiovascular system and respiratory system both under inpatient and outpatient conditions. The sensor comprises a control unit configured to generate a time delay of the synchronization pulse, a probing signal forming circuit, a transmitting and receiving antenna, a probing signal transmitter train, the output of which is connected to the transmitting antenna, a reflected signal receiver circuit, the input of which is connected to the receiving antenna, and a first electronic switch. The input of the first electronic switch is connected to the output of the probing signal forming circuit, and its outputs are connected to the input of the probing signal transmitter circuit and to the reflected signal receiver circuit. The outputs of the channels for processing a reflected signal contained in the reflected signal receiver circuit are connected to a circuit for calculating a respiratory rate and heart rate. The circuit for calculating rates includes two frequency filters, two adders, two signal amplitude calculating units, two signal energy calculating units, two integrators, two comparators, two signal multiplying units, two units for generating a reference signal, second and third electronic switches.

A disadvantage of the device is that the duration of the reference pulse is always equal to the duration of the probing pulse, whereby the reference pulse will always depend on the probing pulse that sets boundaries of the distance sensitivity range in dependence on the occupied bandwidth and resolution of the device, which greatly limits the functionality of the device, reducing the accuracy, reliability and range of the measurements. For instance, to increase the resolution and hence the accuracy of the device, the probing pulse has to be very short, therefore, the reference pulse is very short, and this reduces the operating range of the device. Besides, the construction of the device assumes at least one long UHF communication line (from the first electronic switch either to the probing signal transmitter circuit or to the reflected signal receiver circuit), which, due to rapid attenuation of the UHF signal, limits the maximum allowable distance between the transmitting and receiving antennas in the need for their spacing and imposes additional requirements on PCB material and makes the device relatively expensive.

BRIEF DESCRIPTION OF THE INVENTION

The proposed device can be used for remote non-contact monitoring of vital signs and state of elderly people, patients of sedentary lifestyle, neonates, especially prone to sleep apnea, as well as for monitoring in order to study the phases of sleep, sleep disorders, epileptic aura, wherein monitoring can be as an outpatient (for instance, observation of sleep/wakefulness of a child or an adult, determining of a "turned" state for neonates), and in general in the wards of clinics or medical institutions. Besides, the device can also be used for remote non-contact monitoring of vital signs of animals, for instance, in veterinary medicine, in laboratory studies or in a zoo, in cases where the contact diagnosis is difficult, dangerous or unacceptable, as it may expose an animal to undesirable stress.

The problem to be solved by the claimed invention is to develop a new high efficiency and at the same time, relatively inexpensive device for remote non-contact monitoring of vital signs of a living being to be used in medicine and/or veterinary in conditions when contact diagnosis of a living being is difficult, dangerous or unacceptable.

The present disclosure enables improved measurement accuracy and reliability, increased operating range and reduced likelihood of mistakenly detecting extraneous objects.

The problem is solved and the required technical effect is achieved in a device for remote non-contact monitoring of vital signs of a living being comprising at least one measuring unit, at least one control and data processing unit, and at least one interface unit, wherein the measuring unit is connected to the control and data processing unit, and the control and data processing unit is connected to the interface unit, wherein the measuring unit comprises at least one radio transmitting module, and at least one radio receiving module, wherein the control and data processing unit is configured to generate control pulses for each of the radio transmitting and radio receiving modules delayed for arbitrary time periods between each other, characterized in that each radio transmitting module and/or each radio receiving module contained in the measuring unit is made independent of the other modules, and the control and data processing unit is additionally configured to generate control pulses of arbitrary duration for each of the radio transmitting and radio receiving modules.

In another aspect, the invention is characterized in that each of the radio receiving modules further comprises a UHF reference pulse generator.

In yet another aspect, the invention is characterized in that each of the radio receiving modules comprises a sequentially connected receiving antenna, a low noise amplifier, a phase detector, a band-pass filter and an amplifier, wherein the second input of the phase detector is connected to the output of the UHF generator.

In yet another aspect, the invention is characterized in that the radio transmitting module comprises a sequentially connected UHF generator, an amplifier and a transmitting antenna.

In yet another aspect, the invention is characterized in that each of the radio transmitting and receiving modules are spaced from each other by a distance from 0.0001 m to 20 m. In yet another aspect, the invention is characterized in that the control and data processing unit comprises sequentially interconnected an analog-to-digital converter and a microcontroller.

In yet another aspect, the invention is characterized in that the control and data processing unit further comprises short pulse driver, an input of which is connected to the microcontroller.

In yet another aspect, the invention is characterized in that the short pulse driver outputs are connected to the inputs of each of the UHF generators of the radio receiving and radio transmitting modules of the measuring unit.

In yet another aspect, the invention is characterized in that the analog-digital converter is built into the microcontroller.

In yet another aspect, the invention is characterized in that the control and data processing unit further comprises an external non-volatile memory device connected to the microcontroller.

In yet another aspect, the invention is characterized in that the measuring unit further comprises at least one sensor and an actuating module. In yet another aspect, the invention is characterized in that the sensor is a sensor selected from a group comprising a motion sensor, a sound sensor, a video sensor, a temperature sensor, a humidity sensor, a pressure sensor, a magnetic field sensor, a light sensor, a tactile sensor, an electrical button or a combination thereof.

In yet another aspect, the invention is characterized in that the actuating module is a device selected from a group comprising a sound playback device, a video playback device, a light indicator device, a vibration motor, an electric motor or a combination thereof.

In yet another aspect, the invention is characterized in that the interface unit comprises at least one sensor and an actuating module.

In yet another aspect, the invention is characterized in that the sensor is a sensor selected from a group comprising a motion sensor, a sound sensor, a video sensor, a temperature sensor, a humidity sensor, a pressure sensor, a magnetic field sensor, a light sensor, a touch sensor, an electrical button or a combination thereof. In yet another aspect, the invention is characterized in that the actuating module is a device selected from a group comprising a sound playback device, a video playback device, a light indicator device, a vibration motor, an electric motor or a combination thereof.

In yet another aspect, the invention is characterized in that the measuring unit and the control and data processing unit are arranged in a common enclosure and are interconnected by a wired communication channel, and the control and data processing unit and the interface unit are connected by a wireless communication channel, wherein the interface unit is arranged in a separate enclosure.

In yet another aspect, the invention is characterized in that the measuring unit is located in a separate enclosure and is connected to the control and data processing unit by wireless communication channel, and the control and data processing unit and the interface unit are arranged in a common enclosure and are connected by a wired communication channel.

In yet another aspect, the invention is characterized in that the measuring unit, the control and data processing unit, and the interface unit are arranged in a common enclosure and are interconnected by wired communication channels.

In yet another aspect, the invention is characterized in that the measuring unit, the control and data processing unit, and the interface unit are each located in a separate enclosure and are interconnected by wireless communication channels.

The essential difference of the claimed invention is a new design of the device for remote non-contact monitoring of vital signs of a living being, in particular its radio transmitting and radio receiving modules, as well as the control and data processing unit. In the new device, each radio transmitting module and/or each radio receiving module contained in the measuring unit is made independent of the other modules, and the control and data processing unit is further configured to generate control pulses for each of the radio transmitting and radio receiving modules delayed for arbitrary time periods between each other, that unlike the prototype, cumulatively provides the possibility of independent setting and regulating durations of probing and/or reference pulses, and allows the duration of the probing pulse to be reduced, which leads to the expansion of the frequency band used, higher distance resolution which, in turn, leads to a sharp boundary between the zone of sensitivity and the far dead zone, decreasing the likelihood of mistakenly detecting motion of extraneous objects and interference, allowing for more accurate and reliable determining of the position of the observed subject in space relative to its starting position and simultaneously recording even smaller changes in position of the subject of observation in space relative to the starting position. Moreover, the possibility provided by the new design of the device to generate probing and reference pulses of arbitrary length allows just the duration of the probing pulse to be limited, making the reference pulse arbitrarily long, thereby increasing and at the same time adjusting the operating range of the device. Thus, the new embodiment of the above modules and the new embodiment of the control and data processing unit cumulatively enable the improved accuracy and reliability of measurements while increasing the operating range of the device and decreasing the likelihood of mistakenly detecting extraneous objects, i.e. the claimed technical effect is achieved.

These and other objects, advantages, and features of the invention will become apparent to those skilled in the art from the detailed description and the accompanying drawings. It should be understood, however, that the detailed description and accompanying drawings, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWING(S)

Various exemplary embodiments of the subject matter disclosed herein are illustrated in the accompanying drawings in which like reference numerals represent like parts throughout, and in which.

Figure 1:
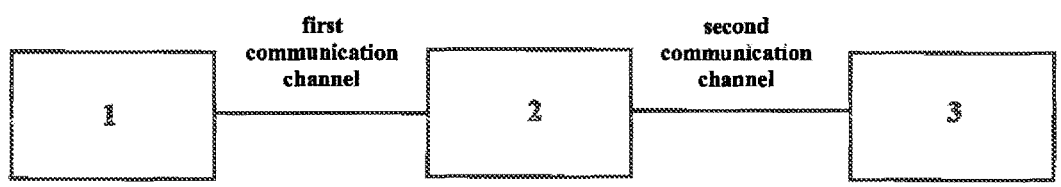
FIG. 1 is a general layout of the main units of the device.

In describing the preferred embodiments of the invention which are illustrated in the drawings, specific terminology will be resorted to for the sake of clarity. However, it is not intended that the invention be limited to the specific terms so selected and it is understood that each specific term includes all technical equivalents which operate in a similar manner to accomplish a similar purpose. For example, the word "connected," "attached," or terms similar thereto are often used. They are not limited to direct connection but include connection through other elements where such connection is recognized as being equivalent by those skilled in the art.

DETAILED DESCRIPTION OF THE PREFERRED EMBODIMENTS

The various features and advantageous details of the subject matter disclosed herein are explained more fully with reference to the non-limiting embodiments described in detail in the following description.

The device for remote monitoring of vital signs of a living being comprises a measuring unit 1, a control and data processing unit 2 and interface unit 3 (FIG. 1). The above units are arranged in a common enclosure (omitted) and are interconnected sequentially by the first and the second wired communication channels, respectively (FIG. 1).

In a particular embodiment of the device, the measuring unit 1 and control and data processing unit 2 can be arranged in a common enclosure (omitted) and interconnected by the first wired communication channel, and interface unit 3 is located in a separate enclosure and connected to the control and data processing unit 2 by the second wireless communication channel (omitted).

In another particular embodiment of the device, the measuring unit 1 can be arranged in a separate enclosure and connected to the control and data processing unit 2 by the first wireless communication channel, the control and data processing unit 2 and the interface unit 3 can be arranged in a separate common enclosure and interconnected by the second wired communication channel (omitted).

In another particular embodiment of the device, all the above units can be arranged in a common enclosure and interconnected by the first and the second wireless communication channels, respectively (omitted).

There can be multiple measuring units 1, control and data processing units 2 and interface units 3 (omitted) depending on the requirements for the specific conditions of the measurements.

Figure 2:
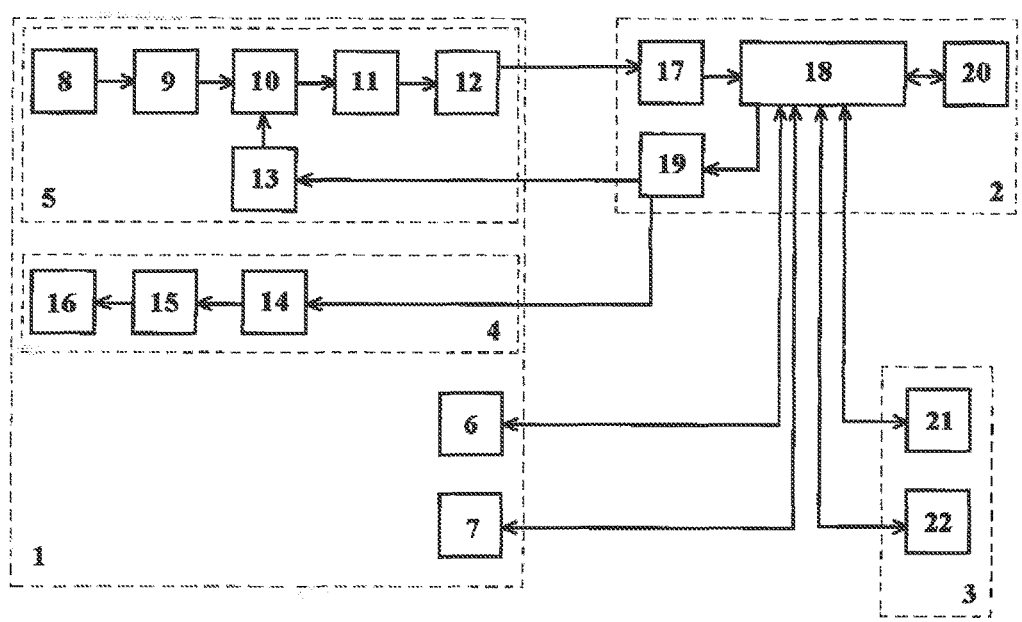
FIG. 2 is a general block diagram of the device.

The measuring unit 1 comprises at least one radio transmitting module 4, at least one radio receiving module 5, and further at least one sensor 6 and the actuating module 7 (FIG. 2).

FIG. 2 shows that the radio receiving module 5 comprises a sequentially connected receiving antenna 8, a low noise amplifier 9, a phase detector 10, a band-pass filter 11, an amplifier 12 and an additional UHF reference pulse generator 13, respectively connected to the phase detector. Radio transmitting module 4 comprises a sequentially connected UHF probing pulse generator 14, an amplifier 15 and a transmitting antenna 16 (FIG. 2).

The UHF probing pulse generator 14 in the radio transmitting unit 4 and the UHF reference pulse generator 13 in the radio receiving module 5 ensure the independence of the modules 4, 5 relatively to each other, which in particular allows a short probing signal to be generated with a bandwidth wider than 500 MHz, which conforms to UWB signal standards, and at the same time a delayed long reference signal can be generated to provide the desired operation range for the device.

The UHF probing pulse generator 14 in the radio transmitting unit 4 and the UHF reference pulse generator 13 in the radio receiving module 5 allow spacing the above radio transmitting and radio receiving modules with respect to each other by a distance from 0.0001 m to 20 m due to the absence of a UHF communication links between them.

Spaced arrangement of the radio transmitting module 4 and radio receiving module 5 from 0.0001 m to 20 m allows for the signal reflected from the subject of observation at a distance from the radio transmitting module 4 to be received, which reduces the level of the direct signal reaching the antenna 8 of the radio receiving module 5 generated by the operation of the radio transmitting module 4 and thereby improves the accuracy and reliability of the measurements.

Spaced arrangement of multiple radio receiving modules (omitted) from 0.0001 m to 20 m, made independent of each other, provides, firstly, a considerable reduction in the likelihood that simultaneously in all receiving modules phase of the reflected signal will fall into a low phase sensitivity area of the phase detectors; secondly, a significant reduction in the likelihood of a decrease in simultaneous reflected signal level in all radio receiving modules due to interference, which also further improves the accuracy, integrity and reliability of measurements.

The spaced arrangement of multiple radio transmitting modules (omitted) from 0.0001 m to 20 m, made independent of each other, provides the possibility of obtaining information on the nature of the motion of the subject of observation in three dimensions, thereby further improving the accuracy, integrity and reliability of the measurements.

In a particular embodiment of the device, there can be multiple radio transmitting modules 4 as well as radio receiving modules 5 (omitted), wherein each of them is made independent of the other modules. Having multiple radio transmitting modules 4 and multiple radio receiving modules 5 allows measurements at different angles and in different planes, which further enables the extension of the observation area, information on the nature of the motion of the subject of observation in three dimension space to be obtained, and readings of several radio transmitting and/or radio receiving modules to be correlated, further improving the accuracy and reliability of the measurements by duplication.

The sensor 6 can be a motion sensor, a sound sensor, a video sensor, a temperature sensor, a humidity sensor, a pressure sensor, a magnetic field sensor, a light sensor, a touch sensor, an electrical button or a combination thereof (omitted).

The actuating module 7 is a device selected from a group comprising a sound playback device, a video playback device, a light indicator device, a vibration motor, an electric motor or a combination thereof (omitted).

The control and data processing unit 2 comprises an interconnected analog-to-digital converter 17 and a microcontroller 18 (FIG. 2). In a particular embodiment of the device, the analog-to-digital converter 17 can be built into the microcontroller 18 (omitted). The control and data processing unit 2 further comprises a short pulse driver 19 and an external non-volatile memory device 20, the inputs of which are connected to the microcontroller 18 (FIG. 2). Input of the analog-to-digital converter 17 is connected to the output of amplifier 12 (the first communication channel). The microcontroller 18 is connected to the sensor 6 and the actuating module 7 of the measuring unit 1 (the first communication channel). Outputs of the short pulse driver 19 are connected to inputs of the UHF generators 13 and 14 (the first communication channel), wherein the modules 4, 5 are made independent of each other. Such a design of the device while measuring allows simultaneous adjustment of the occupied bandwidth, distance resolution and sensitivity area of the device (observation area).

The interface unit 3 comprises at least one sensor 21 and actuating module 22 connected to the microcontroller 18 (the second communication channel) (FIG. 2). The sensor 21 can be a motion sensor, a sound sensor, a video sensor, a temperature sensor, a humidity sensor, a pressure sensor, a magnetic field sensor, a light sensor, a touch sensor, an electrical button or a combination thereof (omitted). The actuating module 22 can be a device selected from a group comprising a sound playback device, a video playback device, a light indicator device, a vibration motor, an electric motor or a combination thereof (omitted).

The claimed device operates as follows.

The microcontroller 18 generates a clock signal, which is fed to the short pulse driver 19. The short pulse driver 19 generates a set of pulses with determined durations and mutual delays for the UHF generators 13, 14 of modules 4 and 5 that, unlike the prototype, allows:

the delay between the probing signal and the reference signal to be set, thereby forming a distance dead zone, and therefore does not accept extraneous signals until the expected detection of the reflected signal, reduces the likelihood of receiving noisy signal, reduces the likelihood of receiving signals from extraneous objects, increases signal-to-noise ratio. Increasing signal-to-noise ratio leads to increased likelihood of deriving the motion path of the subject of observation, increased measurement reliability, increase in the maximum distance of the subject of observation from the device; reduction in the duration of the probing signals, resulting in expansion of the occupied bandwidth, increased distance resolution, and a sharper boundary between the distance sensitivity range of the device and far dead zone;

the duration of the probing signals to be increased, which leads to increased energy of the probing signal, and increases signal-to-noise ratio;

the duration of reference signals to be reduced, which leads to narrowing the observation area, a decrease in the time of receiving extraneous signals, and hence a reduction in the likelihood of receiving noisy signal, and the likelihood of receiving signals from extraneous objects, thus increasing the signal-to-noise ratio;

the duration of reference signals to be increased, which leads to expansion of the observation area, and thereby increasing the likelihood of detecting the subject.

The signal from the UHF generator 14 of the radio transmitting module 4 is fed through the amplifier 15 to the transmitting antenna 16 and radiated into a space towards the observed subject (omitted). The radio signal reflected from the observed subject is received by the receiving antenna 8 of the module 5. Then the above signal is amplified by the low noise amplifier 9 and fed to the input of the phase detector 10. The signal of the UHF generator 13 is fed to the reference (second) input of the phase detector 10. At the output of the phase detector 10 the signal is generated, the shape of which is proportional to the change in the phase difference of signals on both inputs of the phase detector 10. The required range of the signal is allocated by the band-pass filter 11, amplified by amplifier 12 and fed to the control and data processing unit 2. There the signals are digitized by the analog-to-digital converter 17 and sent for processing to the microcontroller 18. The microcontroller 18 processes signals to derive the states of the observed subject. The processing results can be written to the volatile memory device 20. In addition to processing of the above radio signals, the microcontroller 18 processes data and events received from one or more sensors (6, 21) arranged both in the measurement unit 1 and in the interface unit 3. The microcontroller 18 also controls various actuating modules (7, 22) arranged both in the measurement unit 1, and in the interface unit 3, respectively.

The claimed device can be used, for instance, to prevent the crying of a child at the moment of awakening. Preventing crying of a child at the moment of awakening is performed by deriving the state of the child through the nature of his/her motion via the claimed device sensitive enough to register the child's breathing, and by transmitting information on motion activity of the child through the second communication channel to the interface unit 3. Determination of the "sleep" state takes place if a periodic signal of chest movement in a frequency range characteristic for infants (30-60 breaths per minute) is observed; determining the "awakening" state takes place if during a period of time t (for instance, 30 sec.) there is observed a stochastic signal with the amplitude greater than the amplitude of the periodic breathing signal is observed. Given the fact that the child starts moving before opening the eyes, then early alert to the observer (mom) on the "awakening" state will allow him (her) to come to the child before the child finds himself alone and starts to cry.

The claimed device can also be used, for instance, to inform parents on the presence of a child in a crib. Informing parents on the presence of the child in the crib is performed by deriving the state of the child through the nature of his/her motion via the claimed device sensitive enough to register the child's breathing, and by transmitting information on the motion activity of the child through the second communication channel to the interface unit 3. Determination of the "sleep" state takes place if a periodic signal of chest movement in a frequency range characteristic for infants (30-60 breaths per minute) is observed; determination of the "awakening" state takes place if during a period of time t (for instance, 30 sec.) a stochastic signal with the amplitude greater than the amplitude of the periodic breathing signal is observed. Determining the "missing" state takes place if during the time ti (for instance, 20 seconds) a stochastic signal which does not exceed the amplitude of the periodic breathing signal is observed. Determination of the above states will allow the observer at any time of the day or night to get information on whether the child is in the crib, whether he/she is asleep or awake, and make a decision at his/her discretion (for instance, one can wake up at night in silence, and instead of going to check the child, just look at the interface unit 3, and see that the child is asleep; or, after the "missing" signal from the actuating module 22, promptly react to the state of apnea which has occurred and prevent sudden infant death syndrome (SIDS) through mechanical action on the child). The claimed device can also be used, for instance, to inform the observer on the state of a patient in a bed. Informing the observer on the state of a patient in a bed is performed by deriving the state of the patient through the nature of his/her motion via the claimed device sensitive enough to register the patient's breathing, and by transmitting information on motion activity of the patient through the second communication channel to the interface unit 3. Determination of the "sleep" state takes place if a periodic signal of chest movement in a frequency range characteristic for an adult (4-20 breaths per minute) is observed; determination of the "awakening" state takes place if during a period of time t (for instance, 30 sec.) a stochastic signal with the amplitude greater than the amplitude of the periodic breathing signal is observed. Determining the "missing" state takes place if during the time tx (for instance, 20 seconds) a stochastic signal which does not exceed the amplitude of the periodic breathing signal is observed. Determination of the above states will allow the observer at any time of the day or night to get information on whether the patient is in the bed, whether he/she is asleep or awake, and make a decision at his/her discretion (for instance, one may decide not to disturb the patient while the latter is sleeping, or, after the "missing" signal promptly react to the unauthorized leaving of the bed).

To implement the claimed invention both in general, and in particular configurations, the measuring unit 1, the control and data processing unit 2 and the interface unit 3 can basically be materials, elements and units that are well-known and used in the field of remote monitoring of vital signs of living beings.

The device can be arranged in a variety of modifications, so as to include additional elements and/or units of the prior art such as frequency filters, amplifiers, time-delay lines and modulators in the radio transmitting module, frequency filters, amplifiers, time-delay lines, phase-shifting circuits, multipliers, detectors and demodulators in the radio receiving module.

The present invention is not limited to the disclosed configurations, and on the contrary covers various modifications and variations within the essence and scope of the stated claims.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

What is claimed:

1. A device for remote non-contact monitoring of vital signs of a living being comprising at least one measuring unit, at least one control and data processing unit, and at least one interface unit, wherein the measuring unit is connected to the control and data processing unit, and the control and data processing unit is connected to the interface unit, wherein the measuring unit comprises at least one radio transmitting module, and at least one radio receiving module, wherein the control and data processing unit is configured to generate control pulses for each of the radio transmitting and radio receiving modules delayed for arbitrary time periods between each other, wherein each radio transmitting module and/or each radio receiving module contained in the measuring unit is made independent of the other modules, and the control and data processing unit is additionally configured to generate control pulses of arbitrary duration for each of the radio transmitting and radio receiving modules.

2. The device of claim 1, wherein each of the radio receiving modules further comprises a UHF reference pulse generator.

3. The device of claim 2, wherein each of the radio receiving modules comprises a sequentially connected receiving antenna, a low noise amplifier, a phase detector, a band-pass filter and an amplifier, wherein the second input of the phase detector is connected to the output of the UHF generator.

4. The device of claim 1, wherein the radio transmitting module comprises a sequentially connected UHF generator, an amplifier and a transmitting antenna.

5. The device of claim 1, wherein each of the radio transmitting and radio receiving modules are spaced from each other by a distance from 0.0001 m to 20 m.

6. The device of claim 1, wherein the control and data processing unit comprises an analog-to-digital converter and a microcontroller, connected sequentially.

7. The device of claim 6, wherein the control and data processing unit further comprises a short pulse driver, an input of which is connected to the microcontroller.

8. The device of claim 7, wherein each of the radio receiving modules further comprises a UHF reference pulse generator, each of the radio transmitting modules comprises a UHF generator, and the short pulse driver outputs are connected to the inputs of each of the UHF generators of the radio receiving and radio transmitting modules of the measuring unit.

9. The device of claim 6, wherein the analog-digital converter is built into the microcontroller.

10. The device of claim 6, wherein the control and data processing unit further comprises an external non-volatile memory device connected to the microcontroller.

11. The device of claim 1, wherein the measuring unit further comprises at least one sensor and one actuating module.

12. The device of claim 11, wherein the sensor is a sensor selected from a group comprising a motion sensor, a sound sensor, a video sensor, a temperature sensor, a humidity sensor, a pressure sensor, a magnetic field sensor, a light sensor, a touch sensor, an electrical button or a combination thereof.

13. The device of claim 10, wherein the actuating module is a device selected from a group comprising a sound playback device, a video playback device, a light indicator device, a vibration motor, an electric motor or a combination thereof.

14. The device of claim 1, wherein the interface unit comprises at least one sensor and one actuating module.

15. The device of claim 14, wherein the sensor is a sensor selected from a group comprising a motion sensor, a sound sensor, a video sensor, a temperature sensor, a humidity sensor, a pressure sensor, a magnetic field sensor, a light sensor, a touch sensor, an electrical button or a combination thereof.

16. The device of claim 15, wherein the actuating module is a device selected from a group comprising a sound playback device, a video playback device, a light indicator device, a vibration motor, an electric motor or a combination thereof.

17. The device of claim 1, wherein the measuring unit and the control and data processing unit are arranged in a common enclosure and are interconnected by a wired communication channel, and the control and data processing unit and the interface unit are connected by a wireless communication channel, wherein the interface unit is arranged in a separate enclosure.

18. The device of claim 1, wherein the measuring unit is located in a separate enclosure and is connected to the control and data processing unit by a wireless communication channel, and the control and data processing unit and the interface unit are arranged in a common enclosure and are connected by a wired communication channel.

19. The device of claim 1, wherein the measuring unit, the control and data processing unit, and the interface unit are arranged in a common enclosure and are interconnected by wired communication channels.

20. The device of claim 1, wherein the measuring unit, the control and data processing unit, and the interface unit are each located in a separate enclosure and are interconnected by wireless communication channels.

* * * * *